United States Patent [19]

Schwarz et al.

[11] Patent Number: 5,334,136
[45] Date of Patent: Aug. 2, 1994

[54] SYSTEM FOR TREATING BLOOD PROCESSED IN A CARDIOPULMONARY BYPASS MACHINE AND ULTRASOUND FILTRATION APPARATUS USEFUL THEREIN

[76] Inventors: Karl Schwarz, 90 Gorham St., Canandaijea, N.Y. 14424; Richard S. Meltzer, 22 Westland Ave., Rochester, N.Y. 14618; Charles C. Church, 309 N. 16th St., Oxford, Miss. 38655

[21] Appl. No.: 467,444

[22] Filed: Jan. 19, 1990

[51] Int. Cl.⁵ ............................................. A61M 1/30
[52] U.S. Cl. ........................................ 604/4; 604/20
[58] Field of Search ................................ 604/4-6, 604/19, 20; 210/748; 55/15, 277

[56] References Cited

U.S. PATENT DOCUMENTS

| | | |
|---|---|---|
| 2,620,894 | 12/1952 | Peterson . |
| 3,109,721 | 11/1963 | Zenner . |
| 3,650,094 | 3/1972 | Goodwin . |
| 3,853,500 | 12/1974 | Gassmann . |
| 4,055,491 | 10/1977 | Furedi . |
| 4,205,966 | 6/1980 | Horikawa . |
| 4,398,925 | 8/1983 | Trinh . |
| 4,526,038 | 7/1985 | Box . |
| 4,540,399 | 4/1985 | Litzie et al. ............................ 604/4 |
| 4,556,467 | 12/1985 | Kuhn . |
| 4,612,018 | 9/1986 | Tsubol . |
| 4,666,595 | 5/1987 | Graham . |
| 4,689,986 | 9/1987 | Carson . |
| 4,728,368 | 3/1988 | Pedziwiatr ...................... 210/748 X |
| 4,820,620 | 4/1989 | Hayden ................................ 604/4 |
| 4,923,598 | 5/1990 | Schäl ................................... 604/5 |
| 4,961,860 | 10/1990 | Masri .................................. 210/748 |
| 4,983,189 | 1/1991 | Peterson et al. ................ 210/748 X |
| 5,006,266 | 4/1991 | Schram .............................. 210/748 |

FOREIGN PATENT DOCUMENTS

| | | |
|---|---|---|
| 1189458 | 6/1985 | Canada . |
| 0167406 | 1/1986 | European Pat. Off. . |

OTHER PUBLICATIONS

Belyanin et al. *Russian Engineering Journal,* vol. 56, pp. 51-55 (1976).

Primary Examiner—Robert A. Hafer
Assistant Examiner—Sam Rimell
Attorney, Agent, or Firm—M. Lukacher

[57] ABSTRACT

A system for reducing post-cardiopulmonary bypass encephalopathy due to microembolization of the brain of a patient with gaseous microbubbles (less than 40 microns in diameter) occurring during open-heart surgery using a cardiopulmonary bypass machine by passing a stream of blood from the patient through an ultrasonic traveling wave which propagates across the stream without reflection and sweeps the blood clean of the microbubbles without inducing blood cell trauma. The blood passes through a chamber between an input port and a filtrate exit port. An ultrasonic beam is projected so that a pressure maximum of the main lobe of the beam is centered at the filtrate exit port. The microbubbles are carried by the traveling wave to a waste exit port in the chamber downstream of the input port. To prevent establishment of resonance conditions, reflections and traveling waves the chamber may be submerged in a liquid bath and a body of acoustic absorbent material disposed at an end of the chamber opposite to the end into which the ultrasonic beam is projected.

19 Claims, 1 Drawing Sheet

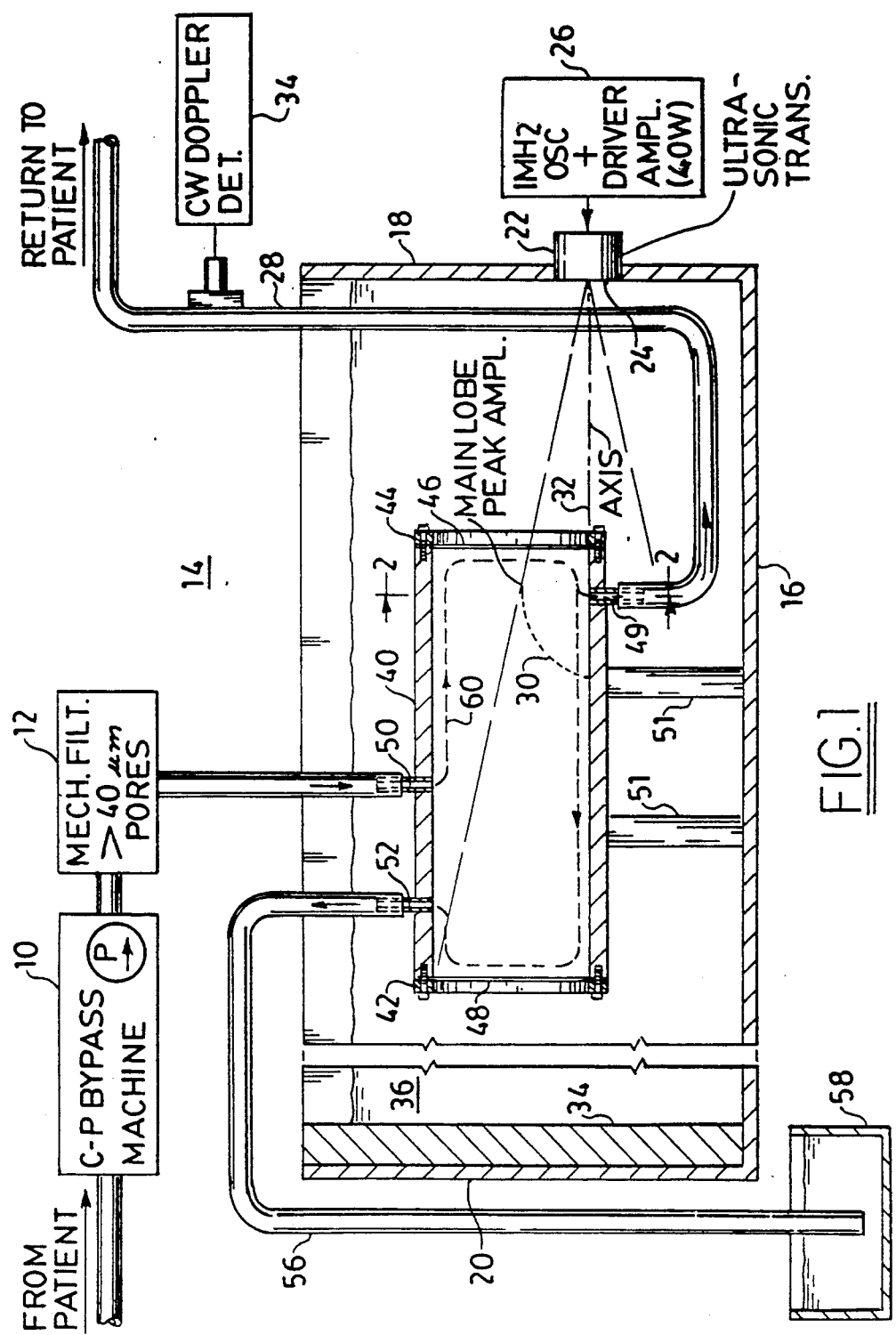

SYSTEM FOR TREATING BLOOD PROCESSED IN A CARDIOPULMONARY BYPASS MACHINE AND ULTRASOUND FILTRATION APPARATUS USEFUL THEREIN

The present invention relates to an improved system (method and apparatus) for the atraumatic filtering of fragile liquids, such as blood, to remove particles, such as microbubbles, which are produced by cardiopulmonary bypass machines in the course of open-heart surgery, and particularly to ultrasonic fluid filtration apparatus useful in such a system.

The invention is especially suitable for reducing microbubble embolization during cardiopulmonary bypass surgery. Aspects of the invention will be found applicable generally for fluid filtration, especially of fragile fluids, such as blood which can be damaged by mechanical filtering or intense pressure variations.*

*"Fragile blood elements include, but are not limited to: red+white blood cells, platelets and certain plasma proteins.

Open-heart surgery is a modality which has been effective in many types of heart disease. Such surgery involves extracorporeal oxygenation through the use of a cardiopulmonary bypass machine. Following open-heart surgery neurologic and neuropsychiatric abnormalities have been noted. Encephalopathy appears to be the most common postoperative neurologic complication. This syndrome is believed to result from continuous diffuse microembolization of the brain with particulate and gas microemboli which are produced in the operation of the cardiopulmonary bypass machine* including the associated parts such as plastic tubing and mechanical filters which handle the blood.**

* (also commonly referred to as the "heart-lung machine")
**Surgery involving the use of a heart-lung machine is commonly referred to as "open-heart surgery".

Current mechanical filter technology is limited to a pore size (usually above 40 micrometers) that is much larger than that of the cerebral capillaries (7 microns diameter). Smaller pore sizes of mechanical filters present problems of increasing the fluid (hemodynamic) resistance on the pumps in the cardiopulmonary bypass machine, and the more serious problem of inducing blood trauma. It is also believed that small pore size mechanical filters in use today introduce microbubbles, rather than remove them from the blood.

It is the principal feature of this invention to provide an improved system (method and apparatus) for decreasing the incidence of diffuse neurologic damage after open-heart surgery. Another feature is to provide for the nondestructive or disruptive filtration of microbubbles from fragile liquids such as blood which circulate through a cardiopulmonary bypass circuit from and then returning to the patient undergoing open-heart surgery.

Separation of particles in liquids through the use of ultrasonic energy has been proposed. However, techniques which have been proposed are unsatisfactory for treating fragile fluids such as blood atraumatically. Particularly, such techniques are designed to cause reflections and standing waves in the body of liquid to be filtered. Standing waves cause particles and microbubbles to collect at acoustic pressure nodes and thereby remain in the liquid. The traumatic effects which are induced also result from pressure nodes established by the ultrasonic energy in the fluid which disrupt the blood elements causing trauma to blood cells and platelets. Because of such disruption, the blood cannot be returned to the patient because of toxicity effects. In addition ultrasound-induced blood trauma may be caused by cavitation at the pressure peaks.

It is a feature of the invention to provide an acoustic filtration system wherein reflected and standing waves which can cause damage to fragile liquids such as blood is avoided. Another feature of the invention is to provide an improved acoustic (particularly ultrasonic) filtration system where traveling waves are produced without reflection so as to push particles suspended in the liquid, such as microbubbles in blood, and sweep them from suspension in the liquid. It is still another feature of the invention to provide an improved acoustic filtration system which presents substantially less fluid resistance to the transmission of liquids than mechanical filters capable of filtering particles of equal or even greater particle size than the acoustic filter provided by the invention. When used in treatment of blood in a cardiopulmonary bypass circuit, the filtration system features less hemodynamic resistance than the bypass machine and other plumbing and elements in the circuit.

Briefly described, the system of the invention is useful in treating blood obtained from a patient (arterial line blood) undergoing cardiac bypass surgery which blood has been processed by a cardiopulmonary bypass machine (a heart-lung machine). The method is operative to filter microbubbles which may be produced by the machine before returning the blood to the patient. The method is carried out by generating an ultrasonic traveling wave, which is substantially free of reflections, through a stream of the blood to sweep the microbubbles (40 microns and less in size) out of the stream before the blood is returned to the patient. The stream is confined in a chamber, which is preferably completely filled with blood. The chamber has an inlet port and outlet ports for filtrate and for waste (the microbubbles). The complete filling of the chamber avoids any trapped air which may have adverse bioeffects on the blood. The chamber also enables the flow to decelerate as it is pumped, for example by pumps in the heart-lung machine. A beam containing the ultrasonic wave is projected into tile chamber through an acoustically transparent window. This beam is diverging, and is preferably the main lobe of a flat plate radiator of an ultrasonic transducer. The beam is incident on the blood stream transversely; portions of said beam making an acute angle of incidence with the stream. The lobe is centered at the filtrate exit port. As the wave travels through the chamber (axially), it sweeps the microbubbles from the stream (viz. an "acoustic radiation force"). This is believed due to the gas having a much lower mass and higher acoustic compliance (lower acoustic impedance) than the blood constituents. The bubbles, exit the chamber and out of the waste port, which may be returned to a point of lower pressure than the pressure in the chamber as applied by the pump in the heart-lung machine. The flitrate, which is clear of microbubbles, is then returned to the patient. The chamber may be submerged in a bath of water and a body of acoustic absorbing material disposed in the bath opposite to an acoustically transparent window through which the beam exits from the chamber. The bath and acoustic absorbing body prevent reflections and the establishment of any standing waves in the chamber.

The foregoing and other features, objects and advantages of the invention as well as a presently preferred embodiment thereof and the best mode now known for practicing the invention will become more apparent from a reading of the following description in connection with the accompanying drawings in which:

FIG. 1 is an elevational view in cross section which schematically illustrates the invention; and FIG. 2 is a cross section taken along the line 2—2 in FIG. 1.

Referring to the drawings there is shown a circuit which receives arterial line blood from a patient undergoing cardiopulmonary bypass surgery. This blood is processed in a cardiopulmonary (C-P) bypass machine 10 having an internal pump. The blood is provided with extracorporeal oxygenation in the machine 10. Large size particles (greater than 40 microns) are removed by a mechanical filter 12.

The blood is then treated for the removal of microbubbles of less than 40 micron (micrometers) size in an ultrasonic filtration system 14. The system includes a tank 16 having opposite end walls 18 and 20. A commercial ultrasonic transducer 22 having a planar radiator in its frontal surface 24 is mounted in the end wall 18. This transducer is driven by an oscillator and driver amplifier circuit 26. In a preferred embodiment the frequency of the oscillator signal is 1 $MH_z$ and the driver amplifier has a 40 watt output which drives the transducer 22. The frequency which is selected depends upon the size of microbubbles to be filtered. It has been found that 1 $MH_z$ is suitable for filtering microbubbles in the 40 micron and less range (e.g. 4-32 microns) as are produced by the bypass machine 10, the mechanical filter 12 and the other lines in the circuit.

The transducer has a radiation pattern with a main lobe 30 which is symmetrical about an axis 32. The main lobe has a peak amplitude which is in the plane of the section 2—2. It has been found that the pressure in the main lobe varies approximately plus and minus 3 Bar and that such pressure is sufficient to sweep the microbubbles in the blood so that blood clear of microbubbles can be returned to the patient via an outlet line 28 of the circuit. Cavitation does not occur in the blood.

The presence and absence of microbubbles in the filtrate may be measured by a C.W. Doppler detector 34, the probe 36 of which is connected to the outlet line 28. All of the lines may be polycarbonate or polyethylene tubes of the type that are used conventionally in cardiopulmonary bypass circuits. These lines may for example be ⅜ inch inside diameter lines.

The end wall 20 which is opposite the wall 18 in which the transducer 22 is mounted is covered by a plate 34 of acoustic absorbent material such as Rho-C rubber. Panels of similar absorbent material may be used to line the bottom and side walls and other end wall 18. The tank also contains a bath 36 of water thereby avoiding any air/liquid interfaces which might cause reflections. The plate 34 absorbs the ultrasonic energy in the beam from the transducer 22 and prevents the formation of any standing waves. Accordingly, only a traveling wave of ultrasonic energy is launched and propagates through the bath 36.

The filtration system uses a chamber 40, which in the illustrated embodiment is made of an acrylic tube which is sealed at its ends by acoustically transparent windows 46 48, clamped by rings 42 and 44 to the opposite ends of the tube 40. The tube in an embodiment of the invention may be 5 centimeters in inside diameter and approximately 18 centimeters long. The tank 16 which is used in the exemplary illustrated embodiment of the invention was 50 centimeters long, 21 centimeters high and 20 centimeters wide. The longitudinal cross section of the chamber 40 is shown in FIG. 1. The design of the chamber may be rectangular rather than circular in cross section.

The acoustically transparent windows 46 and 48 may be Mylar thin film (e.g. 3-4 mils) membranes. These membranes are transparent to tile ultrasonic waves. The chamber is supported on a framework which is illustrated as two brackets 51. This framework enables the chamber 40 to be positioned in the tank so that the main lobe 30 has its peak amplitude centered (the axis 32 of the lobe will intersect) at the entrance to the filtrate outlet port 49. There is also an inlet port 50 and a waste outlet port 52. The ports are defined by holes in the tube defining the chamber 40 in which liquid tight couplings are inserted (screwed in). These couplings are connected to the tubes of the circuit. Barbs (not shown) provide a liquid tight connection. The filtrate exit port 49 is closest to the end of the chamber 40 which faces the transducer 22. The inlets and outlets 49, 50 and 52 have their axes in the same longitudinal, diametral plane through the longitudinal axis of the tube defining the chamber 40. The filtrate exit port 49 and the inlet 50 are diametrically opposite but offset from each other for example by 10 centimeters. The axis through the filtrate outlet port 49 may be approximately 10 centimeters from the radiator 24 of the transducer 22. Adjustments to optimize the operation may be readily made by moving the chamber on its supports 51.

The waste outlet port 52 is connected by a tube 56 to a reservoir 58 located below the tank 16 so that the pressure at the waste outlet port 52 is less than the pressure in the chamber 40.

In operation the chamber 40 is completely filled with blood so that no air/blood interface exists in the chamber. The flow of the stream of blood follows the side and front wall (provided by the window 46) of the chamber and is shown by the dash lines 60. This flow is transverse to the beam of ultrasonic energy. Because the beam diverges, portions thereof are at an acute incidence angle to the stream. The traveling wave in the beam sweeps the microbubbles towards the rear end (at the window 48) of the chamber 40 and the microbubbles flow through the waste exit port 52 into the reservoir 58. The reservoir may be much larger than shown or a sump for disposal of liquid medical wastes.

From the foregoing description it will be apparent that there has been provided an improved system for treating blood during cardiopulmonary bypass surgery so as to alleviate postoperative encephalopathy due to microembolization of the patient's brain by microbubbles and to ultrasonic filtration apparatus useful therein. Modifications in the herein described system and apparatus as well as other uses and applications thereof, are within the scope of the invention, and will undoubtedly suggest themselves to those skilled in the art. Accordingly, the foregoing description should be taken as illustrative and not in a limiting sense.

We claim:

1. The method of treating blood obtained from a patient undergoing cardiac bypass surgery and processed by a cardiopulmonary bypass machine to filter microbubbles therein before returning the blood to the patient which comprises the steps of generating and transmitting through a stream of said blood an ultrasonic travelling wave which is substantially free of reflections to sweep said bubbles out of said stream.

2. The method according to claim 1 further comprising the step of confining said stream into a volume having an inlet and second and first outlets for waste flow including said microbubbles and return of said blood to said patient, respectively, said first outlet, said inlet and said second outlet being disposed successively in the direction of said traveling wave.

3. The method according to claim I further comprising directing said traveling wave in a beam which is incident on said stream in a direction transverse to said stream so that portions of said beam intersect said stream at an acute angle.

4. The method according to claim 2 wherein said first outlet has an entrance from said volume and further comprising the step of directing said beam so that it has a centerline which is immediately adjacent to said entrance and fans outwardly therefrom.

5. The method according to claim 4 further comprising the step of absorbing said waves after they leave said volume thereby preventing reflection and standing waves in said volume.

6. The method according to claim 1 further comprising the step of reducing the hemodynamic resistance between said machine and said patient to much less than the hemodynamic resistance from said patient through said machine and back to said patient while filtering said microbubbles.

7. The method according to claim 1 further comprising maintaining the acoustic pressure of said wave below cavitation pressure.

8. The method according to claim 7 wherein said pressure is maintained to approximately 3 Bar.

9. The method according to claim 1 further comprising measuring the rate of passage of microbubbles in said stream past after said treatment by said traveling wave and before return to said patient.

10. The method according to claim 2 further comprising the step of filling said volume entirely with blood of said stream thereby eliminating the presence of an interface with said blood and said air on opposite sides thereof in said chamber.

11. Apparatus for filtering a stream of a fragile liquid, such as blood, which comprises a source of ultrasonic vibrations, means for continuously projecting said vibrations as a traveling wave across said stream without reflections and without standing waves to sweep microbubbles and like particles from said stream.

12. The apparatus according to claim 11 wherein said stream has an inlet, a first outlet and a second outlet for said microbubbles and like particles, and for said stream, respectively, said outlets having entrances thereto, said projecting means including means for projecting said beam in a lobe having a pressure maximum in which the entrance to said second outlet is centrally disposed.

13. The apparatus according to claim 11 further comprising a chamber having an inlet, a filtrate outlet and a waste outlet for said microbubbles and like particles, said outlets having entrances thereto from said chamber, said stream extending from said inlet to said filtrate outlet, said projecting means including means providing a diverging beam having an axis, said axis extending across the entrance to said filtrate outlet in the immediate proximity thereof.

14. The apparatus according to claim 13 wherein said filtrate outlet is closer to said source than said inlet and said waste outlet is further from said source than said inlet.

15. The apparatus according to claim 11 further comprising means for maintaining said chamber completely filled in its entire volume with said liquid.

16. The apparatus according to claim 14 wherein said filtrate outlet is opposite to said inlet and said waste outlet is alongside said inlet.

17. The apparatus according to claim 13 wherein said chamber has a wall and ends spaced from each other along the length of said chamber, acoustically transparent entry and exit windows extending across each of said ends, said beam axis extending in a direction between said entry and exit windows.

18. The apparatus according to claim 17 further comprising a body of acoustic absorbing material disposed facing said exit window.

19. The apparatus according to claim 18 further comprising means for providing a liquid bath in which said chamber is submerged, said bath extending to said body of acoustic absorbing material.

* * * * *